(12) United States Patent
Fujihira et al.

(10) Patent No.: US 7,659,416 B2
(45) Date of Patent: Feb. 9, 2010

(54) MONOMOLECULAR CONDUCTIVE COMPLEX, CONDUCTIVE SELF-ASSEMBLED FILM AND ASSEMBLY OF ELECTRODE COMPOSED OF METAL AND SEMICONDUCTOR MAKING USE OF THE SAME

(75) Inventors: Masamichi Fujihira, Yokohama (JP); Fumie Sato, Fujisawa (JP); Yuuki Takayama, Funabashi (JP); Go Ono, Funabashi (JP)

(73) Assignees: Tokyo Institute of Technology, Tokyo (JP); Nissan Chemical Industries, Ltd., Tokyo (JP)

( * ) Notice: Subject to any disclaimer, the term of this patent is extended or adjusted under 35 U.S.C. 154(b) by 167 days.

(21) Appl. No.: 11/886,725

(22) PCT Filed: Mar. 17, 2006

(86) PCT No.: PCT/JP2006/305351
§ 371 (c)(1),
(2), (4) Date: Feb. 8, 2008

(87) PCT Pub. No.: WO2006/101028
PCT Pub. Date: Sep. 28, 2006

(65) Prior Publication Data
US 2009/0036698 A1  Feb. 5, 2009

(30) Foreign Application Priority Data
Mar. 23, 2005 (JP) ................ 2005-08428

(51) Int. Cl.
C07F 1/00 (2006.01)
C07F 3/00 (2006.01)
C07F 15/00 (2006.01)
C07C 327/00 (2006.01)
C07C 395/00 (2006.01)

(52) U.S. Cl. ............ 556/110; 556/113; 556/118; 556/130; 556/136; 556/138; 558/251; 562/899

(58) Field of Classification Search ............... 556/110, 556/113, 118, 130, 136, 138; 558/251; 562/899
See application file for complete search history.

(56) References Cited
U.S. PATENT DOCUMENTS

| | | | |
|---|---|---|---|
| 2003/0103367 A1 | 6/2003 | Aeppli et al. | |
| 2003/0104637 A1 | 6/2003 | Aeppli et al. | |
| 2003/0130358 A1 | 7/2003 | Sato et al. | |
| 2004/0176643 A1 | 9/2004 | Sato et al. | |

FOREIGN PATENT DOCUMENTS

| | | |
|---|---|---|
| JP | 2003-168788 A | 6/2003 |
| JP | 2004-058260 A | 2/2004 |
| JP | 2004-119618 A | 4/2004 |
| JP | 2004-136377 A | 5/2004 |
| JP | 2004-175742 A | 6/2004 |
| JP | 2005-033184 A | 2/2005 |
| WO | WO-01/68595 A1 | 9/2001 |

OTHER PUBLICATIONS

Prall, Metthias et al., Journal of Computational Chemistry, 22(13), 2001, pp. 1605-1614.
S. Ye et al., *J. Chem. Soc., Faraday Trans.*, 1996, 92(20), 3813-3821.
H. Skulason et al., *Langmuir*, 1998, 14, 5834-5840.
M. A. Reed et al., *Science*, vol. 278, Oct. 10, 1997, 252-254.
J. Chen et at., *Science*, vol. 286, Nov. 19, 1999, 1550-1552.
B. Xu et al., *Science*, vol. 301, Aug. 29, 2003, 1221-1223.
A. Szuchmacher Blum et al., *Applied Physics Letters*, vol. 82, No. 19, May 12, 2003, 3322-3324.
A. Salomon et al., *Adv. Matter.*, vol. 15, No. 22, Nov. 17, 2003, 1881-1890.
X. Xiao et al., *Agnew. Chem. Int. Ed.*, 2004, 43, 6148-6152.
X. L. Li et al., *Surface Science*, 573 (2004) 1-10.
R. L. McCreery, *Chem. Mater.*, 2004, 16, 4477-4496.
J. Nara et al., *Journal of Chemical Physics*, vol. 121, No. 13, Oct. 1, 2004, 6485-6492.
T. Tada et al., *J. Am. Chem. Soc.*, 2004, 126, 14182-14189.
S-H. Ke et al., *J. Am. Chem. Soc.*, 2004, 126, 15897-15904.
W. Haiss et al., *Phys. Chem. Chem. Phys.*, 2004, 6, 4330-4337.
J. He et al., *J. Am. Chem. Soc.*, 2005, 127, 1384-1385.
B. Xu et al., *J. Am. Chem. Soc.*, 2005, 127, 2386-2387.
S. Yamaguchi et al., *J. Org. Chem.*, 1998, 63, 10060-10062.
T. Hamada et al., *J. Am. Chem. Soc.*, 1999, 121, 7342-7344.

*Primary Examiner*—Porfirio Nazario Gonzalez
(74) *Attorney, Agent, or Firm*—Birch, Stewart, Kolasch & Birch, LLP

(57) ABSTRACT

Enediyne compounds of the formula: (1) characterized in that the structure thereof is very simple and the production process is easy, and that the molecular length thereof is shorter than those of compounds having been proposed. Consequently, electrode assemblies comprising any of these enediyne compounds are highly promising in the application to nanomolecular wiring (nanomolecular wire) whose production has been difficult.

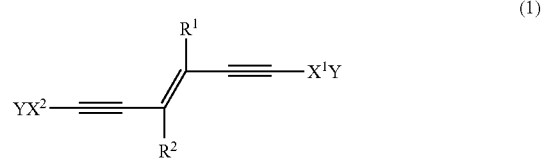

(1)

8 Claims, 1 Drawing Sheet

MONOMOLECULAR CONDUCTIVE COMPLEX, CONDUCTIVE SELF-ASSEMBLED FILM AND ASSEMBLY OF ELECTRODE COMPOSED OF METAL AND SEMICONDUCTOR MAKING USE OF THE SAME

TECHNICAL FIELD

This invention relates to a monomolecular conductive complex, a conductive self-assembled film, and an electrode junction making use of the same and composed of a metal and a semiconductor. More specifically, it is concerned with a monomolecular conductive complex formed of a compound having the enediyne structure, a conductive self-assembled film, and an electrode junction formed by chemical bonding of the compound and a metal, metal oxide or semiconductor.

BACKGROUND ART

Active research and development work have been conventionally performed on compounds containing heteroatoms such as sulfur atoms as monomolecular complexes and self-assembled films on various substrates. To apply these monomolecular complexes and self-assembled films to electronic devices, a great deal of research and development work have also been conducted concerning compounds capable of imparting electrical conductivity to monomolecular complexes and self-assembled films.

In addition, research and development work have also been performed about compounds having the above-described complex-forming and self-assembling function, and also about junctions between compounds obtained by imparting electrical conductivity to such compounds and electrodes composed of metals or semiconductors.

As a conductivity-imparted compound for self-assembled films, for example, there is known 2-(11-mercaptoundecyl)-hydroquinone having a quinone moiety as an electron acceptor structure at an end thereof (see Non-Patent Document 1).

Also known is a mixture of bis(10-(2-(2,5-cyclohexadien-1,4-diylidene)dimalononitrile))decyl)disulfide having a tera-cyanoquinodimethane moiety as an electron acceptor structure at an end thereof and N,N,N-trimethyl-N-(10-mercapto)decyl-1,4-phenylenediamine having a tetramethylphenylenediamine moiety as an electron donor structure at an end thereof (see Non-Patent Document 2).

Further, compounds represented by the following formula (3) are also known. As specific compounds, there are known compounds of the formula (3) in which $R_{11}$ to $R_{14}$ are each a methyl group, 2-cyanoethyl group or a hydrogen atom and compounds of the formula (3) in which $R_{11}$ is a hydrogen atom and $R_{12}$ to $R_{14}$ are each a 2-cyanoethyl group (see Patent Document 1). These compounds are advantageous from the standpoint of industrial applications, as their production processes are simple and easy.

[Chemical Formula 1]

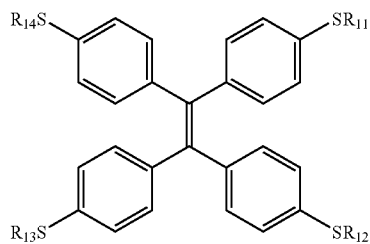

(3)

wherein $R_{11}$ to $R_{14}$ are each independently a hydrogen atom, a substituted or unsubstituted $C_1$ to $C_6$ alkyl group, a substituted or unsubstituted $C_2$ to $C_6$ alkenyl group, a substituted or unsubstituted $C_1$ to $C_6$ aryl group, a bromine atom, or a chlorine atom.

In addition, compounds represented by the following formula (4) are also known (see Patent Document 2). These compounds are also advantageous from the standpoint of industrial applications, as their production processes are simple and easy.

[Chemical Formula 2]

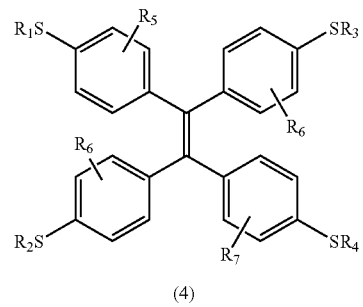

(4)

wherein $R^1$ to $R^4$ each independently represent an organic group, at least one of them represents an organic group, which is a divalent connecting group including at least one of an arylene group and an alkylene group and has at an end thereof a binding group capable of covalently or coordinatively forming a bond with a metal surface, metal oxide surface or semiconductor surface, and $R^5$ to $R^8$ each independently represent a halogen atom, a $C_1$ to $C_3$ alkyl group or a $C_1$ to $C_3$ alkoxy group.

As a process for the fabrication or production of electrodes composed of metals and a semiconductors by making use of various monomolecular complexes or self-assembled films or conductivity-imparted various monomolecular complexes or self-assembled films while taking their applications to electronic devices, for example, so-called molecular wiring or the like is known (see Patent Documents 3 to 7 and Non-Patent Documents 3 to 16).

As disclosed in the respective documents referred to in the above, a variety of compounds have been reported to date as monomolecular conductive complexes or compounds for conductive self-assembled films. However, their chemical structures are considerably limited so that many of them lack versatility and are functionally insufficient. Moreover, their production processes are complex and, when industrial applications to electronic devices and the like are taken into consideration, none of them have practical utility.

Patent Document 1:
WO 01/68595 Pamphlet
Patent Document 2:
JP-A 2004-175742
Patent Document 3:
JP-A 2003-168788
Patent Document 4:
JP-A 2004-058260
Patent Document 5:
JP-A 2004-119618
Patent Document 6:
JP-A 2004-136377
Patent Document 7:
JP-A 2005-033184

Non-Patent Document 1:
J. Chem. Soc., Faraday Trans., 92, 3813 (1996)
Non-Patent Document 2:
Langmuir, 14, 5834 (1998)
Non-Patent Document 3:
Science, 278, 10 Oct., 252 (1997)
Non-Patent Document 4:
Science, 286, 19 Nov., 1550 (1999)
Non-Patent Document 5:
Science, 301, 29 Aug., 1221 (2003)
Non-Patent Document 6:
Applied Physics Letters, 82, 19, 3322 (2003)
Non-Patent Document 7:
Advanced Materials, 15, 22, 1881 (2003)
Non-Patent Document 8:
Angew. Chem. Int. Ed., 2004, 43, 6148
Non-Patent Document 9:
Surface Science, 573, 1 (2004)
Non-Patent Document 10:
Chem. Mater., 2004, 16, 4477
Non-Patent Document 11:
Journal of Chemical Physics, 121, 13, 6485 (2004)
Non-Patent Document 12:
J. Am. Chem. Soc., 2004, 126, 14182
Non-Patent Document 13:
J. Am. Chem. Soc., 2004, 126, 15897
Non-Patent Document 14:
Phys. Chem. Chem. Phys., 2004, 6, 4330
Non-Patent Document 15:
J. Am. Chem. Soc., 2005, 127, 1384
Non-Patent Document 16:
J. Am. Chem. Soc., 2005, 127, 2386

DISCLOSURE OF THE INVENTION

Problems to be Solved by the Invention

With the foregoing circumstances in view, an object of the present invention provides a monomolecular conductive complex, an enediyne compound usable as a conductive self-assembled film, and an electrode junction making use of the enediyne compound.

Means for Solving the Problems

The present inventors have proceeded with an extensive investigation to achieve the above object. As a result, it was found that π-conjugated compounds each containing an enyne-type, preferably enediyne-type π-conjugated chain and having, at opposite ends of its molecule, binding groups capable for forming covalent bonds or coordinate bonds with a surface of a metal, metal oxide or semiconductor, such as group 16 atoms such as sulfur or selenium atoms, are suited as conductive compounds for self-assembled films, leading to the completion of the present invention.

In addition, the present inventors fabricated metal-metal electrodes by using monomolecular conductive complexes and conductive self-assembled films composed of such enediyne compounds, and studied their characteristics. As a result, it was found that they have sufficient applicability to electronic devices, also leading to the completion of the present invention.

Described specifically, the present invention provides:
1. An enediyne compound characterized by being represented by the formula (1):

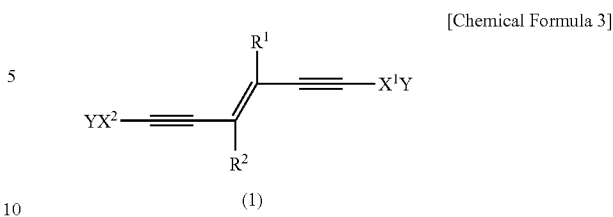

[Chemical Formula 3]

(1)

wherein $R^1$ and $R^2$ each independently represent a hydrogen atom, halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, $C_1$ to $C_{10}$ alkoxy $C_1$ to $C_{10}$ alkyl group, $C_1$ to $C_1$ alkyl carbonyl $C_1$ to $C_{10}$ alkyl group, di $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, W-substituted or unsubstituted aryl group, W-substituted or unsubstituted arylalkyl group, W-substituted or unsubstituted aryloxy group, W-substituted or unsubstituted arylthio group, W-substituted or unsubstituted monoarylamino group, W-substituted or unsubstituted diarylamino group, W-substituted or unsubstituted tri $C_1$ to $C_{10}$ aryl silyl group, W-substituted or unsubstituted arylcarbonyl group, or W-substituted or unsubstituted aryloxycarbonyl group; $X^1$ and $X^2$ each independently represent a sulfur atom or selenium atom; Y represents a hydrogen atom, $C_1$ to $C_{10}$ alkyl group, $C_1$ to $C_{10}$ alkoxy group, $C_1$ to $C_1$ alkyl carbonyl group, $C_1$ to $C_{10}$ alkoxy carbonyl group, W-substituted or unsubstituted aryl group, W-substituted or unsubstituted arylalkyl group, W-substituted or unsubstituted $C_1$ to $C_{10}$ aryl carbonyl group, or W-substituted or unsubstituted $C_1$ to $C_{10}$ aryloxy carbonyl group; W represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, Z-substituted or unsubstituted phenyl group, Z-substituted or unsubstituted naphthyl group, or Z-substituted or unsubstituted biphenyl group; and Z represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, or $C_1$ to $C_{10}$ alkoxy carbonyl group.

2. An enediyne compound as described above under 1, wherein $R^1$ and $R^2$ each independently represent a hydrogen atom, halogen atom, cyano group, nitro group, $C_1$ to $C_{10}$ alkyl group, halo $C_1$ to $C_{10}$ alkyl group, $C_1$ to $C_{10}$ alkoxy group, di $C_1$ to $C_{10}$ alkyl amino group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above); $X^1$ and $X^2$ each independently represent a sulfur atom; and Y represents a hydrogen atom, $C_1$ to $C_{10}$ alkyl group, $C_1$ to $C_{10}$ alkoxy group, $C_1$ to $C_{10}$ alkyl carbonyl group, $C_1$ to $C_{10}$ alkoxy carbonyl group, W-substituted or unsubstituted aryl group, W-substituted or unsubstituted arylalkyl group, W-substituted or unsubstituted $C_1$ to $C_{10}$ aryl carbonyl group, or W-substituted or unsubstituted $C_1$ to $C_{10}$ aryloxy carbonyl group (in which W has the same meaning as defined above).

3. An enediyne compound as described above under 2, wherein $R^1$ and $R^2$ each independently represent a hydrogen atom, $C_1$ to $C_1$ alkyl group, halo $C_1$ to $C_{10}$ alkyl group, $C_1$ to $C_{10}$ alkoxy $C_1$ to $C_{10}$ alkyl group, $C_1$ to $C_{10}$ alkyloxy carbonyl $C_1$ to $C_{10}$ alkyl group, di $C_1$ to $C_1$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above); and Y represents a hydrogen atom or $C_1$ to $C_{10}$ alkyl carbonyl group.

4. An electrode junction represented by a formula (2) characterized in that an enediyne compound is covalently or coordinatively bonded at opposite ends thereof with a surface of a metal, metal oxide or semiconductor:

[Chemical Formula 4]

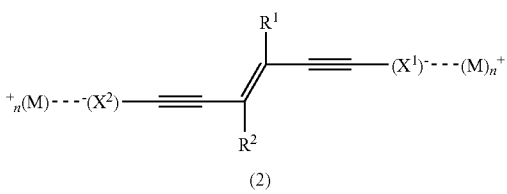

(2)

wherein $R^1, R^2, X^1$ and $X^2$ have the same meanings as defined above; and each M is a metal atom derived from the metal, metal oxide or semiconductor, and represents Au, Ag, Cu, Pd, Fe, Hg, Ga or In.

5. An electrode junction as described above under 4, wherein $R^1$ and $R^2$ each independently represent a hydrogen atom, halogen atom, cyano group, nitro group, $C_1$ to $C_{10}$ alkyl group, halo $C_1$ to $C_{10}$ alkyl group, $C_1$ to $C_{10}$ alkoxy group, di $C_1$ to $C_{10}$ alkyl amino group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above); and $X^1$ and $X^2$ each independently represent a sulfur atom.

6. An electrode junction as described above under 5, wherein, $R^1$ and $R^2$ each independently represent a hydrogen atom, $C_1$ to $C_{10}$ alkyl group, halo $C_1$ to $C_{10}$ alkyl group, $C_1$ to $C_{10}$ alkoxy $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above).

7. An electrode junction as described above under 6, wherein the enediyne compound is covalently or coordinatively bonded at the opposite ends thereof with a surface of a metal or metal oxide; and each M is a metal atom derived from the metal or metal oxide, and represents Au, Ag, Cu, Pd, Fe, Hg, Ga or In.

8. An electrode junction as described above under 7, wherein, the enediyne compound is covalently or coordinatively bonded at the opposite ends thereof with a surface of a metal; and each M is a metal atom derived from the metal, and represents Au, Ag, Cu, Pd, Fe, Hg, Ga or In.

Effects of the Invention

The enediyne compound of the present invention, which is represented by the formula (1) having the π-conjugated system, has the enediyne structure, and has, at opposite ends of its molecule, binding groups capable of forming covalent bonds or coordinate bonds with a surface of a metal, metal oxide or semiconductor, such as group 16 atoms such as sulfur or selenium atoms. It readily binds via covalent bonds or coordinate bonds a metal surface, metal oxide surface or semiconductor surface as an electrode to afford an electrode junction represented by the formula (2).

With respect to the electrode junction, its characteristics as molecular wiring was investigated. As a result, it was confirmed to have better characteristics than conventional molecular wiring compounds.

Further, the enediyne compound of the present invention has a very simple structure, and its production process is also simple and easy. Moreover, it has a characteristic that it has a shorter molecule length compared with the compounds proposed to date. For these characteristic features, electrode junctions composed of the enediyne compound according to the present invention are highly expected to find applications as nanomolecular wiring the fabrication of which have heretofore been difficult, and are considered to have a high industrial utility value.

BEST MODE FOR CARRYING OUT THE INVENTION

Figure 1:
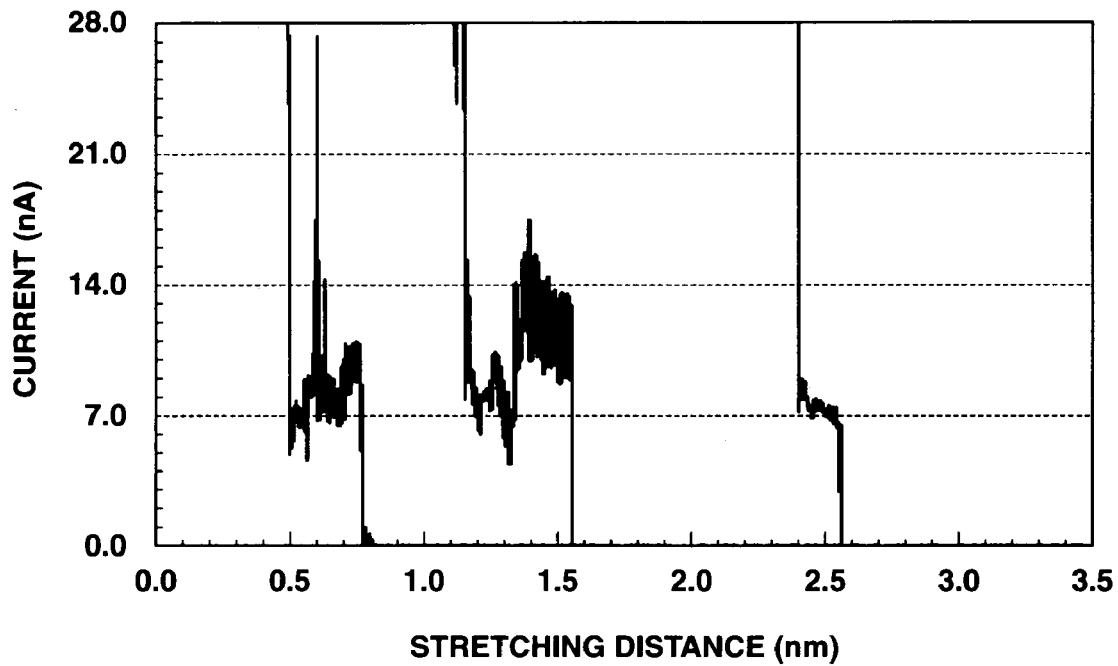
FIG. 1 A graph showing conductance steps of an enediyne-dithiol obtained in Example 1.

The present invention will hereinafter be described in further detail.

It is to be noted that in this specification, "n" means normal, "i" means iso, "s" means secondary, "t" means tertiary, "c" means cyclo, "o" means ortho, "m" means metha, and "p" means para.

$R^1$ and $R^2$ in the above-described formulas (1) and (2) each independently represent a hydrogen atom, halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, W-substituted or unsubstituted aryl group, W-substituted or unsubstituted arylalkyl group, W-substituted or unsubstituted aryloxy group, W-substituted or unsubstituted arylthio group, W-substituted or unsubstituted monoarylamino group, W-substituted or unsubstituted diarylamino group, W-substituted or unsubstituted tri $C_1$ to $C_{10}$ aryl silyl group, W-substituted or unsubstituted arylcarbonyl group, or W-substituted or unsubstituted aryloxycarbonyl group.

Among these, it is preferred that $R^1$ and $R^2$ each independently represent a hydrogen atom, halogen atom, cyano group, nitro group, $C_1$ to $C_{10}$ alkyl group, halo $C_1$ to $C_{10}$ alkyl group, $C_1$ to $C_{10}$ alkoxy group, di $C_1$ to $C_{10}$ alkyl amino group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above), especially a hydrogen atom, $C_1$ to $C_{10}$ alkyl group, halo $C_1$ to $C_{10}$ alkyl group, $C_1$ to $C_{10}$ alkoxy $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above).

$X^1$ and $X^2$ each independently represent a sulfur atom or selenium atom. A sulfur atom is particularly preferred because a self-assembled film can be readily formed on a metal, metal oxide or semiconductor surface.

Y in the formula (1) represents a hydrogen atom, $C_1$ to $C_{10}$ alkyl group, $C_1$ to $C_{10}$ alkoxy group, $C_1$ to $C_{10}$ alkyl carbonyl group, $C_1$ to $C_{10}$ alkoxy carbonyl group, W-substituted or unsubstituted aryl group, W-substituted or unsubstituted arylalkyl group, W-substituted or unsubstituted $C_1$ to $C_{10}$ aryl carbonyl group, or W-substituted or unsubstituted $C_1$ to $C_{10}$ aryloxy carbonyl group (W has the same meaning as defined above). For easy synthesis and easy formation of a junction with a metal, metal oxide or semiconductor, a hydrogen atom or a $C_1$ to $C_{10}$ alkyl carbonyl group is preferred, with a $C_1$ to $C_{10}$ alkyl carbonyl group being particularly preferred.

Further, W represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, Z-substituted or unsubstituted phenyl group, Z-substituted or unsubstituted naphthyl group, or Z-substituted or unsubstituted biphenyl group; and Z represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, or $C_1$ to $C_{10}$ alkoxy carbonyl group.

Each M in the formula (2) is a metal atom, which has been derived from the metal, metal oxide or semiconductor and to which the enediyne compound is bound at the opposite ends thereof. Each M specifically represents Au, Ag, Cu, Pd, Fe, Hg, Ga or In, with Au, Cu or In being preferred.

A description will next be made about specific examples of the substituent groups on the compounds represented by the formulas (1) and (2).

Specific example of the $C_1$ to $C_{10}$ alkyl group include methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl, n-decyl, and the like.

Specific examples of the $C_1$ to $C_{10}$ alkenyl group include $CH=CH_2$, $CH=CHMe$, $CH=CHEt$, $CH=CMe_2$, $CH=CEt_2$, $CMe=CH_2$, $CMe=CHMe$, $CMe=CMe_2$, $CH_2CH=CH_2$, $CH_2CH=CHMe$, $CH_2CH=CHEt$, $CH_2CMe=CH_2$, $CH_2CH_2CH=CH_2$, $CH_2CH_2CH=CHMe$, $CH_2CH=CMe_2$, $CHMeCH=CH_2$, $CH_2CMe=CHMe$, $CHMeCH=CHMe$, $CH_2CMe=CHEt$, $CH_2CH_2CH=CMe_2$, $CH_2CMe=CMe_2$, $CH=C=CH_2$, and the like.

Specific examples of the $C_1$ to $C_{10}$ alkynyl group include $C\equiv CMe$, $C\equiv CEt$, $CH_2C\equiv CH$, $CH_2C\equiv CMe$, $CH_2C\equiv CEt$, $CH_2CH_2C\equiv CH$, $CH_2CH_2C\equiv CMe$, $CHMeC\equiv CH$, $CHMeC\equiv CMe$, and the like.

Specific examples of the halo $C_1$ to $C_{10}$ alkyl group include $CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$, and the like.

Specific examples of the $C_1$ to $C_{10}$ alkoxy group include OMe, OEt, OPr-n, OPr-i, OBu-n, OBu-i, OBu-s, OBu-t, OPen-n, $OCHEt_2$, OHex-n, OCHMe(Pr-n), OCHMe(Bu-n), OCHEt(Pr-n), $OCH_2CH_2CHMe_2$, and the like.

Specific examples of the $C_1$ to $C_{10}$ alkylthio group include SMe, SEt, SPr-n, SPr-i, SBu-n, SBu-i, SBu-s, SBu-t, SPen-n, $SCHEt_2$, SHex-n, SCHMe(Pr-n), SCHMe(Bu-n), SCHEt(Pr-n), $SCH_2CH_2CHMe_2$, and the like.

Specific examples of the mono $C_1$ to $C_{10}$ alkyl amino group include NHMe, NHEt, NHPr-n, NHPr-i, NHBu-n, NHBu-i, NHBu-s, NHBu-t, NHPen-n, $NHCHEt_2$, NHHex-n, and the like.

Specific examples of the di $C_1$ to $C_{10}$ alkyl amino group include $NMe_2$, $NEt_2$, $N(Pr-n)_2$, $N(Pr-i)_2$, $N(Bu-n)_2$, $N(Bu-i)_2$, $N(Bu-s)_2$, $N(Bu-t)_2$, $N(Pen-n)_2$, $N(CHEt_2)_2$, $N(Hex-n)_2$, and the like.

Specific examples of the tri $C_1$ to $C_{10}$ alkyl silyl group include $SiMe_3$, $SiEt_3$, $Si(Pr-n)_3$, $Si(Pr-i)_3$, $Si(Bu-n)_3$, $Si(Bu-i)_3$, $Si(Bu-t)_3$, and the like.

Specific examples of the $C_1$ to $C_{10}$ alkyl carbonyl group include C(O)Me, C(O)Et, C(O)Pr-n, C(O)Pr-i, C(O)Bu-n, C(O)Bu-i, C(O)Bu-s, C(O)Bu-t, C(O)Pen-n, $C(O)CHEt_2$, C(O)Hex-n, and the like.

Specific examples of the $C_1$ to $C_{10}$ alkoxy carbonyl group include OC(O)Me, OC(O)Et, OC(O)Pr-n, OC(O)Pr-i, OC(O)Bu-n, OC(O)Bu-i, OC(O)Bu-s, OC(O)Bu-t, OC(O)Pen-n, $OC(O)CHEt_2$, OC(O)Hex-n, and the like.

Specific examples of the $C_1$ to $C_{10}$ alkoxy $C_1$ to $C_{10}$ alkyl group include $CH_2OMe$, $CH_2OEt$, $CH_2OPr-n$, $CH_2OPr-i$, $CH_2CH_2OMe$, $CH_2CH_2OEt$, $CH_2CH_2OPr-n$, $CH_2CH_2OPr-i$, $CH_2CH_2CH_2OMe$, $CH_2CH_2CH_2OEt$, $CH_2CH_2CH_2OPr-n$, $CH_2CH_2CH_2OPr-i$, and the like.

Specific examples of the $C_1$ to $C_{10}$ alkyl carbonyl $C_1$ to $C_{10}$ alkyl group include $CH_2C(O)Me$, $CH_2C(O)Et$, $CH_2C(O)Pr-n$, $CH_2C(O)Pr-i$, $CH_2CH_2C(O)Me$, $CH_2CH_2C(O)Et$, $CH_2CH_2C(O)Pr-n$, $CH_2CH_2C(O)Pr-i$, $CH_2CH_2CH_2C(O)Me$, $CH_2CH_2CH_2C(O)Et$, $CH_2CH_2CH_2C(O)Pr-n$, $CH_2CH_2CH_2C(O)Pr-i$, and the like.

Specific examples of the $C_1$ to $C_{10}$ alkyloxy carbonyl $C_1$ to $C_{10}$ alkyl group include $CH_2C(O)OMe$, $CH_2C(O)OEt$, $CH_2C(O)OPr-n$, $CH_2C(O)OPr-i$, $CH_2CH_2C(O)OMe$, $CH_2CH_2C(O)OEt$, $CH_2CH_2C(O)OPr-n$, $CH_2CH_2C(O)OPr-i$, $CH_2CH_2CH_2C(O)OMe$, $CH_2CH_2CH_2C(O)OEt$, $CH_2CH_2CH_2C(O)OPr-n$, $CH_2CH_2CH_2C(O)OPr-i$, and the like.

Specific examples of the di $C_1$ to $C_{10}$ alkyl amino $C_1$ to $C_{10}$ alkyl group include $CH_2NMe_2$, $CH_2NEt_2$, $CH_2N(Pr-n)_2$, $CH_2N(Pr-i)_2$, $CH_2CH_2NMe_2$, $CH_2CH_2NEt_2$, $CH_2CH_2N(Pr-n)_2$, $CH_2CH_2N(Pr-i)_2$, $CH_2CH_2CH_2NMe_2$, $CH_2CH_2CH_2NEt_2$, $CH_2CH_2CH_2N(Pr-n)_2$, $CH_2CH_2CH_2N(Pr-i)_2$, and the like.

Specific examples of the nitro $C_1$ to $C_{10}$ alkyl group include $CH_2NO_2$, $CH_2CH_2NO_2$, $CH_2CH_2CH_2NO_2$, and the like.

It is to be noted that in the above-description, "Me" means a methyl group, "Et" means an ethyl group, "Pr" means a propyl group, and "Bu" means a butyl group.

Specific examples of the W-substituted or unsubstituted aryl group include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxyphenyl, 2,4,6-trichlorophenyl, 2,4,6-tribromophenyl, 2,4,6-trifluorophenyl, α-naphthyl, β-naphthyl, o-biphenylyl, m-biphenylyl, p-biphenylyl, thiophen-2-yl, thiophen-3-yl, furan-2-yl, furan-3-yl, pyrrol-1-yl, pyrrol-2-yl, pyrrol-3-yl, and the like.

Specific examples of the W-substituted or unsubstituted arylalkyl group include phenylmethyl, o-methylphenylmethyl, m-methylphenylmethyl, p-methylphenylmethyl, o-trifluoromethylphenylmethyl, m-trifluoromethylphenylmethyl, p-trifluoromethylphenylmethyl, p-ethylphenylmethyl, p-i-propylphenylmethyl, p-t-butylphenylmethyl, o-chlorophenylmethyl, m-chlorophenylmethyl, p-chlorophenylmethyl, o-bromophenylmethyl, m-bromophenylmethyl, p-bromophenylmethyl, O-fluorophenylmethyl, p-fluorophenylmethyl, o-methoxyphenylmethyl, m-methoxyphenylmethyl, p-methoxyphenylmethyl, o-trifluoromethoxyphenylmethyl, p-trifluoromethoxyphenylmethyl, o-nitrophenylmethyl, m-nitrophenylmethyl, p-nitrophenylmethyl, o-dimethylaminophenylmethyl, m-dimethylaminophenylmethyl, p-dimethylaminophenylmethyl, p-cyanophenylmethyl, 3,5-dimethylphenylmethyl, 3,5-bistrifluoromethylphenylmethyl, 3,5-dimethoxyphenylmethyl, 3,5-bistrifluoromethoxyphenylmethyl, 3,5-diethylphenylmethyl, 3,5-di-i-propylphenylmethyl, 3,5-dichlorophenylmethyl, 3,5-dibromophenylmethyl, 3,5-difluorophenylmethyl, 3,5-dinitrophenylmethyl, 3,5-dicyanophenylmethyl, 2,4,6-trimethylphenylmethyl, 2,4,6-tristrifluoromethylphenylmethyl, 2,4,6-trimethoxyphenylmethyl, 2,4,6-tristrifluoromethoxyphenylmethyl, 2,4,6-trichlorophenylmethyl, 2,4,6-tribromophenylmethyl, 2,4,6-trifluorophenylmethyl, α-naphthylmethyl, β-naphthylmethyl, o-biphenylylmethyl, m-biphenylylmethyl, p-biphenylylmethyl, thiophen-2-ylmethyl, thiophen-3-ylmethyl, furan-2-ylmethyl, furan-3-ylmethyl, pyrrol-1-ylmethyl, pyrrol-2-ylmethyl, pyrrol-3-ylmethyl, and the like.

Specific examples of the W-substituted or unsubstituted aryloxy group include phenyloxy, o-methylphenyloxy, m-methylphenyloxy, p-methylphenyloxy, o-trifluoromethylphenyloxy, m-trifluoromethylphenyloxy, p-trifluoromethylphenyloxy, p-ethylphenyloxy, p-i-propylphenyloxy, p-t-butylphenyloxy, o-chlorophenyloxy, m-chlorophenyloxy, p-chlorophenyloxy, o-bromophenyloxy, m-bromophenyloxy, p-bromophenyloxy, o-fluorophenyloxy, p-fluorophenyloxy, o-methoxyphenyloxy, m-methoxyphenyloxy, p-methoxyphenyloxy, o-trifluoromethoxyphenyloxy, p-trifluoromethoxyphenyloxy, o-nitrophenyloxy, m-nitrophenyloxy, p-nitrophenyloxy, o-dimethylaminophenyloxy, m-dimethylaminophenyloxy, p-dimethylaminophenyloxy, p-cyanophenyloxy, 3,5-dimethylphenyloxy, 3,5-bistrifluoromethylphenyloxy, 3,5-dimethoxyphenyloxy, 3,5-bistrifluoromethoxyphenyloxy, 3,5-diethylphenyloxy, 3,5-di-i-propylphenyloxy, 3,5-dichlorophenyloxy, 3,5-dibromophenyloxy, 3,5-difluorophenyloxy, 3,5-dinitrophenyloxy, 3,5-dicyanophenyloxy, 2,4,6-trimethylphenyloxy, 2,4,6-tristrifluoromethylphenyloxy, 2,4,6-trimethoxyphenyloxy, 2,4,6-tristrifluoromethoxyphenyloxy, 2,4,6-trichlorophenyloxy, 2,4,6-tribromophenyloxy, 2,4,6-trifluorophenyloxy, α-naphthyloxy, β-naphthyloxy, o-biphenylyloxy, m-biphenylyloxy, p-biphenylyloxy, thiophen-2-yloxy, thiophen-3-yloxy, furan-2-yloxy, furan-3-yloxy, pyrrol-1-yloxy, pyrrol-2-yloxy, pyrrol-3-yloxy, and the like.

Specific examples of the W-substituted or unsubstituted arylthio group include phenylthio, o-methylphenylthio, m-methylphenylthio, p-methylphenylthio, o-trifluoromethylphenylthio, m-trifluoromethylphenylthio, p-trifluoromethylphenylthio, p-ethylphenylthio, p-i-propylphenylthio, p-t-butylphenylthio, o-chlorophenylthio, m-chlorophenylthio, p-chlorophenylthio, o-bromophenylthio, m-bromophenylthio, p-bromophenylthio, o-fluorophenylthio, p-fluorophenylthio, o-methoxyphenylthio, m-methoxyphenylthio, p-methoxyphenylthio, o-trifluoromethoxyphenylthio, p-trifluoromethoxyphenylthio, o-nitrophenylthio, m-nitrophenylthio, p-nitrophenylthio, o-dimethylaminophenylthio, m-dimethylaminophenylthio, p-dimethylaminophenylthio, p-cyanophenylthio, 3,5-dimethylphenylthio, 3,5-bistrifluoromethylphenylthio, 3,5-dimethoxyphenylthio, 3,5-bistrifluoromethoxyphenylthio, 3,5-diethylphenylthio, 3,5-di-i-propylphenylthio, 3,5-dichlorophenylthio, 3,5-dibromophenylthio, 3,5-difluorophenylthio, 3,5-dinitrophenylthio, 3,5-dicyanophenylthio, 2,4,6-trimethylphenylthio, 2,4,6-tristrifluoromethylphenylthio, 2,4,6-trimethoxyphenylthio, 2,4,6-tristrifluoromethoxyphenylthio, 2,4,6-trichlorophenylthio, 2,4,6-tribromophenylthio, 2,4,6-trifluorophenylthio, α-naphthylthio, β-naphthylthio, o-biphenylylthio, m-biphenylylthio, p-biphenylylthio, thiophen-2-ylthio, thiophen-3-ylthio, furan-2-ylthio, furan-3-ylthio, pyrrol-1-ylthio, pyrrol-2-ylthio, pyrrol-3-ylthio, and the like.

Specific examples of the W-substituted or unsubstituted monoarylamino group include phenylamino, o-methylphenylamino, m-methylphenylamino, p-methylphenylamino, o-trifluoromethylphenylamino, m-trifluoromethylphenylamino, p-trifluoromethylphenylamino, p-ethylphenylamino, p-i-propylphenylamino, p-t-butylphenylamino, o-chlorophenylamino, m-chlorophenylamino, p-chlorophenylamino, o-bromophenylamino, m-bromophenylamino, p-bromophenylamino, o-fluorophenylamino, p-fluorophenylamino, o-methoxyphenylamino, m-methoxyphenylamino, p-methoxyphenylamino, o-trifluoromethoxyphenylamino, p-trifluoromethoxyphenylamino, o-nitrophenylamino, m-nitrophenylamino, p-nitrophenylamino, o-dimethylaminophenylamino, m-dimethylaminophenylamino, p-dimethylaminophenylamino, p-cyanophenylamino, 3,5-dimethylphenylamino, 3,5-bistrifluoromethylphenylamino, 3,5-dimethoxyphenylamino, 3,5-bistrifluoromethoxyphenylamino, 3,5-diethylphenylamino, 3,5-di-i-propylphenylamino, 3,5-dichlorophenylamino, 3,5-dibromophenylamino, 3,5-difluorophenylamino, 3,5-dinitrophenylamino, 3,5-dicyanophenylamino, 2,4,6-trimethylphenylamino, 2,4,6-tristrifluoromethylphenylamino, 2,4,6-trimethoxyphenylamino, 2,4,6-tristrifluoromethoxyphenylamino, 2,4,6-trichlorophenylamino, 2,4,6-tribromophenylamino, 2,4,6-trifluorophenylamino, α-naphthylamino, β-naphthylamino, o-biphenylylamino, m-biphenylylamino, p-biphenylylamino, thiophen-2-ylamino, thiophen-3-ylamino, furan-2-ylamino, furan-3-ylamino, pyrrol-1-ylamino, pyrrol-2-ylamino, pyrrol-3-ylamino, and the like.

Specific examples of the W-substituted or unsubstituted diarylamino group include diphenylamino, bis(o-methylphenyl)amino, bis(m-methylphenyl)amino, bis(p-methylphenyl)amino, bis(o-trifluoromethylphenyl)amino, bis(m-trifluoromethylphenyl)amino, bis(p-trifluoromethylphenyl)amino, bis(p-ethylphenyl)amino, bis(p-i-propylphenyl)amino, bis(p-t-butylphenyl)amino, bis(o-chlorophenyl)amino, bis(m-chlorophenyl)amino, bis(p-chlorophenyl)amino, bis(o-bromophenyl)amino, bis(m-bromophenyl)amino, bis(p-bromophenyl)amino, bis(o-fluorophenyl)amino, bis(p-fluorophenyl)amino, bis(o-methoxyphenyl)amino, bis(m-methoxyphenyl)amino, bis(p-methoxyphenyl)amino, bis(o-trifluoromethoxyphenyl)amino, bis(p-trifluoromethoxyphenyl)amino, bis(o-nitrophenyl)amino, bis(m-nitrophenyl)amino, bis(p-nitrophenyl)amino, bis(o-dimethylaminophenyl)amino, bis(m-dimethylaminophenyl)amino, bis(p-dimethylaminophenyl)amino, bis(p-cyanophenyl)amino, bis(3,5-dimethylphenyl)amino, bis(3,5-bistrifluoromethylphenyl)amino, bis(3,5-dimethoxyphenyl)amino, bis(3,5-bistrifluoromethoxyphenyl)amino, bis(3,5-diethylphenyl)amino, bis(3,5-di-i-propylphenyl)amino, bis(3,5-dichlorophenyl)amino, bis(3,5-dibromophenyl)amino, bis(3,5-difluorophenyl)amino, bis(3,5-dinitrophenyl)amino, bis(3,5-dicyanophenyl)amino, bis(2,4,6-trimethylphenyl)amino, bis(2,4,6-tristrifluoromethylphenyl)amino, bis(2,4,6-trimethoxyphenyl)amino, bis(2,4,6-tristrifluoromethoxyphenyl)amino, bis(2,4,6-trichlorophenyl)amino, bis(2,4,6-tribromophenyl)amino, bis(2,4,6-trifluorophenyl)amino, bis(α-naphthyl)amino, bis(β-naphthyl)amino, bis(o-biphenylyl)amino, bis(m-biphenylyl)amino, bis(p-biphenylyl)amino, bis(thiophen-2-yl)amino, bis(thiophen-3-yl)amino, bis(furan-2-yl)amino, bis(furan-3-yl)amino, bis(pyrrol-1-yl)amino, bis(pyrrol-2-yl)amino, bis(pyrrol-3-yl)amino, and the like.

Specific examples of the W-substituted or unsubstituted tri $C_1$ to $C_{10}$ arylsilyl group include triphenylsilyl, tris(o-methylphenyl)silyl, tris(m-methylphenyl)silyl, tris(p-methylphenyl)silyl, tris(o-trifluoromethylphenyl)silyl, tris(m-trifluoromethylphenyl)silyl, tris(p-trifluoromethylphenyl)silyl, tris(p-ethylphenyl)silyl, tris(p-i-propylphenyl)silyl, tris(p-t-butylphenyl)silyl, tris(o-chlorophenyl)silyl, and the like.

Specific examples of the W-substituted or unsubstituted arylcarbonyl group include phenylcarbonyl, o-methylphenylcarbonyl, m-methylphenylcarbonyl, p-methylphenylcarbonyl, o-trifluoromethylphenylcarbonyl, m-trifluoromethylphenylcarbonyl, p-trifluoromethylphenylcarbonyl, p-ethylphenylcarbonyl, p-i-propylphenylcarbonyl, p-t-butylphenylcarbonyl, o-chlorophenylcarbonyl, m-chlorophenylcarbonyl, p-chlorophenylcarbonyl, o-bromophenylcarbonyl, m-bromophenylcarbonyl, p-bromophenylcarbonyl, o-fluorophenylcarbonyl, p-fluorophenylcarbonyl, o-methoxyphenylcarbonyl, m-methoxyphenylcarbonyl, p-methoxyphenylcarbonyl, o-trifluoromethoxyphenylcarbonyl, p-trifluoromethoxyphenylcarbonyl, o-nitrophenylcarbonyl, m-nitrophenylcarbonyl, p-nitrophenylcarbonyl, o-dimethylaminophenylcarbonyl, m-dimethylaminophenylcarbonyl, p-dimethylaminophenylcarbonyl, p-cyanophenylcarbonyl, 3,5-dimethylphenylcarbonyl, 3,5-bistrifluoromethylphenylcarbonyl, 3,5-dimethoxyphenylcarbonyl, 3,5-bistrifluoromethoxyphenylcarbonyl, 3,5-diethylphenylcarbonyl, 3,5-di-i-propylphenylcarbonyl, 3,5-dichlorophenylcarbonyl, 3,5-dibromophenylcarbonyl, 3,5-difluorophenylcarbonyl, 3,5-dinitrophenylcarbonyl, 3,5-dicyanophenylcarbonyl, 2,4,6-trimethylphenylcarbonyl, 2,4,6-tristrifluoromethylphenylcarbonyl, 2,4,6-trimethoxyphenylcarbonyl, 2,4,6-tristrifluoromethoxyphenylcarbonyl, 2,4,6-trichlorophenylcarbonyl, 2,4,6-tribromophenylcarbonyl, 2,4,6-trifluorophenylcarbonyl, α-naphthylcarbonyl, β-naphthylcarbonyl, o-biphenylylcarbonyl, m-biphenylylcarbonyl, p-biphenylylcarbonyl, thiophen-2-ylcarbonyl, thiophen-3-ylcarbonyl, furan-2-ylcarbonyl, furan-3-ylcarbonyl, pyrrol-1-ylcarbonyl, pyrrol-2-ylcarbonyl, pyrrol-3-ylcarbonyl, and the like.

Specific examples of the W-substituted or unsubstituted aryloxycarbonyl group include phenyloxycarbonyl, o-methylphenyloxycarbonyl, m-methylphenyloxycarbonyl, p-methylphenyloxycarbonyl, o-trifluoromethylphenyloxycarbonyl, m-trifluoromethylphenyloxycarbonyl, p-trifluoromethylphenyloxycarbonyl, p-ethylphenyloxycarbonyl, p-i-propylphenyloxycarbonyl, p-t-butylphenyloxycarbonyl, o-chlorophenyloxycarbonyl, m-chlorophenyloxycarbonyl, p-chlorophenyloxycarbonyl, o-bromophenyloxycarbonyl, m-bromophenyloxycarbonyl, p-bromophenyloxycarbonyl, o-fluorophenyloxycarbonyl, p-fluorophenyloxycarbonyl, o-methoxyphenyloxycarbonyl, m-methoxyphenyloxycarbonyl, p-methoxyphenyloxycarbonyl, o-trifluoromethoxyphenyloxycarbonyl, p-trifluoromethoxyphenyloxycarbonyl, o-nitrophenyloxycarbonyl, m-nitrophenyloxycarbonyl, p-nitrophenyloxycarbonyl, o-dimethylaminophenyloxycarbonyl, m-dimethylaminophenyloxycarbonyl, p-dimethylaminophenyloxycarbonyl, p-cyanophenyloxycarbonyl, 3,5-dimethylphenyloxycarbonyl, 3,5-bistrifluoromethylphenyloxycarbonyl, 3,5-dimethoxyphenyloxycarbonyl, 3,5-bistrifluoromethoxyphenyloxycarbonyl, 3,5-diethylphenyloxycarbonyl, 3,5-di-i-propylphenyloxycarbonyl, 3,5-dichlorophenyloxycarbonyl, 3,5-dibromophenyloxycarbonyl, 3,5-difluorophenyloxycarbonyl, 3,5-dinitrophenyloxycarbonyl, 3,5-dicyanophenyloxycarbonyl, 2,4,6-trimethylphenyloxycarbonyl, 2,4,6-tristrifluoromethylphenyloxycarbonyl, 2,4,6-trimethoxyphenyloxycarbonyl, 2,4,6-tristrifluoromethoxyphenyloxycarbonyl, 2,4,6-trichlorophenyloxycarbonyl, 2,4,6-tribromophenyloxycarbonyl, 2,4,6-trifluorophenyloxycarbonyl, α-naphthyloxycarbonyl, β-naphthyloxycarbonyl, o-biphenylyloxycarbonyl, m-biphenylyloxycarbonyl, p-biphenylyloxycarbonyl, thiophen-2-yloxycarbonyl, thiophen-3-yloxycarbonyl, furan-2-yloxycarbonyl, furan-3-yloxycarbonyl, pyrrol-1-yloxycarbonyl, pyrrol-2-yloxycarbonyl, pyrrol-3-yloxycarbonyl, and the like.

Preferred examples of the enediyne compound of the present invention can include the following compounds, although the present invention shall not be limited to them.

[Chemical Formula 5]

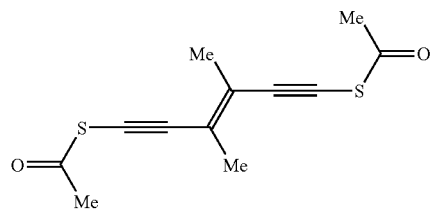

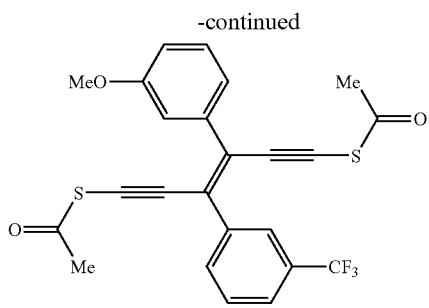
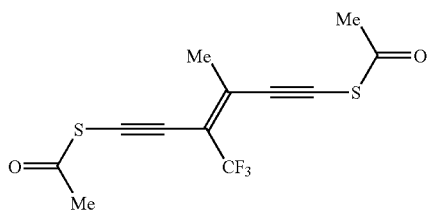
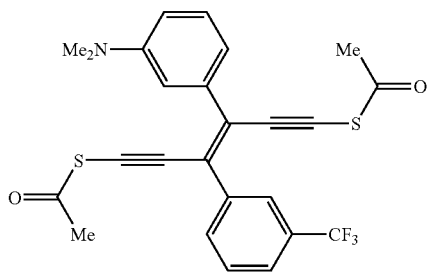
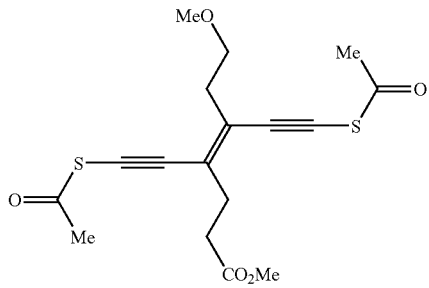
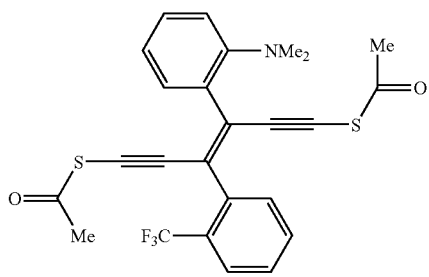
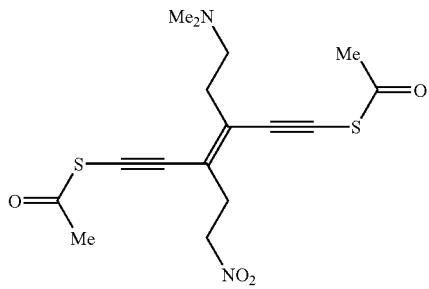
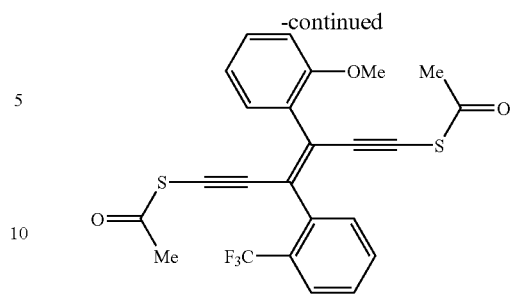
(1) Production Process of Enediyne Compound
An enediyne compound represented by the following formula (5) and useful as a monomolecular conductive complex and also in a conductive self-assembled film can be synthesized, for example, in the following manner.
[Chemical Formula 6]
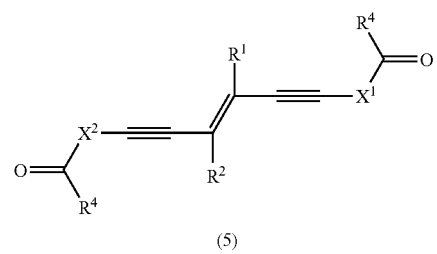
(5)
[Chemical Formula 7]
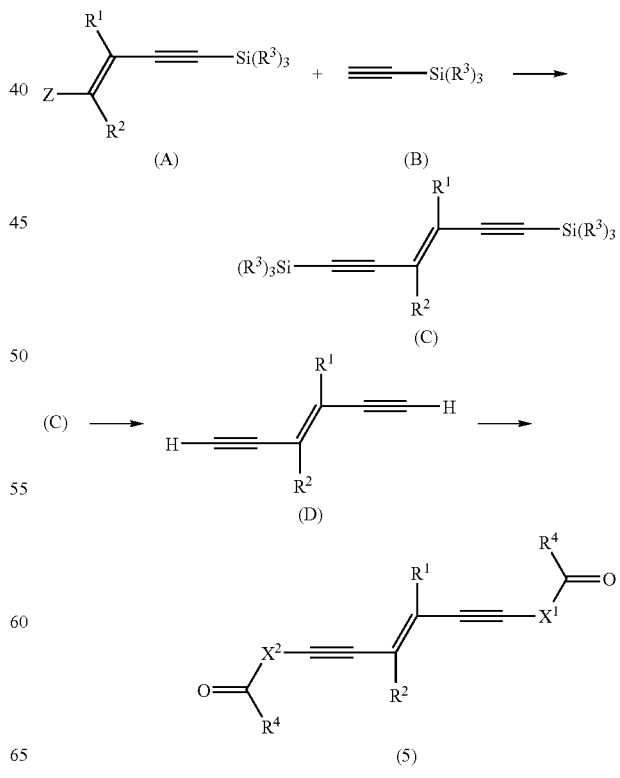

wherein $R^1$, $R^2$ and X have the same meanings as defined above, $R^3$ represents a $C_1$ to $C_6$ alkyl group or aryl group, $R^4$ represents a $C_1$ to $C_{10}$ alkyl group or aryl group, and Z represents a chlorine atom, bromine atom or iodine atom.

Described specifically, a halogenated enyne derivative (A) and a silylated acetylene (B) are subjected to the Sonogashira reaction in the presence of a palladium catalyst to synthesize an intermediate (C), which is subsequently converted into a corresponding desilylated product (D). Using this terminal acetylene compound (D), the target compound (5) can be obtained.

As the palladium catalyst, those of various structures can be used. However, use of a so-called low-valence palladium complex is preferred, with a zero-valence complex with a tertiary phosphine or tertiary phosphite contained as a ligand being particularly preferred. It is also possible a suitable precursor which can be readily converted into a zero-valence complex in the reaction system. Further, a complex which does not contain any tertiary phosphine or tertiary phosphite as a ligand may be mixed with a tertiary phosphine or tertiary phosphate to form a low-valence complex with the tertiary phosphine or tertiary phosphate contained as a ligand.

Illustrative of the tertiary phosphine or tertiary phosphite as a ligand are triphenylphosphine, diphenylmethylphosphine, phenyldimethylphosphine, 1,2-bis(diphenylphosphino)ethane, 1,3-bis(diphenylphosphino)propane, 1,4-bis(diphenylphosphino)butane, 1,1'-bis(diphenylphosphino)ferrocene, trimethylphosphite, triethylphosphite, triphenylphosphite, and the like. A complex containing two or more of these ligands in combination can also be used suitably.

It is also a preferred embodiment of the catalyst to use a palladium complex, which does not contain any tertiary phosphine or tertiary phosphate, and/or a palladium complex, which contains a tertiary phosphine or tertiary phosphate, and the above-mentioned ligand in combination.

As a complex which does not contain any tertiary phosphine or tertiary phosphite and is usable in combination with the ligand, bis(benzylideneacetone)palladium, palladium acetate or the like can be mentioned. As a complex which already contains a tertiary phosphine or tertiary phosphite, on the other hand, dimethylbis(triphenylphosphine)palladium, dimethylbis(diphenylmethylphosphine)palladium, (ethylene)bis(triohenylphosphine)palladium, tetrakis(triphenylphosphine)palladium or the like can be mentioned, although the complex shall not be limited to the above-exemplified one.

The amount of the palladium catalyst to be used may be a so-called catalytic amount. Typically, it is sufficient to use the palladium in an amount of 20 mole % or smaller based on the substrate (B). Usually, its amount is 5 mole % or smaller.

No particular limitation is imposed on a reaction solvent for use in the above-described production process, insofar as it is stable and inert under the reaction conditions and does not interfere with the reaction. Examples include solvents such as water; alcohols (for example, methanol, ethanol, propanol, butanol, octanol, etc.); Cellosolves (for example, methoxyethanol, ethoxyethanol, etc.); aprotic polar organic solvents (for example, dimethylformamide, dimethyl sulfoxide, dimethylacetamide, tetramethylurea, sulfolane, N-methylpyrrolidone, N,N-dimethylimidazolidinone, etc.); ethers (for example, diethyl ether, diisopropyl ether, t-butyl methyl ether, tetrahydrofuran, dioxane, etc.); aliphatic hydrocarbons (for example, pentane, hexane, c-hexane, octane, decane, decalin, petroleum ether, etc.); aromatic hydrocarbons (benzene, chlorobenzene, o-dicyclobenzene, nitrobenzene, toluene, xylene, mesitylene, tetralin, etc.); halogenated hydrocarbon (for example, chloroform, dichloromethane, dichloroethane, carbon tetrachloride, etc.); ketones (acetone, methyl ethyl ketone, methyl butyl ketone, methyl isobutyl ketone, etc.); lower fatty acid esters (for example, methyl acetate, ethyl acetate, butyl acetate, methyl propionate, etc.); alkoxyalkanes (for example, dimethoxyethane, diethoxyethane, etc.); and nitriles (for example, acetonitrile, propionitrile, butyronitrile, etc.).

These solvents can be chosen as needed in view of the probability that the reaction will occur. The above-described solvents can be used either singly or in combination. It is to be noted that the above-described solvents can be used as non-aqueous solvents by using an appropriate dehydrating agent or desiccant agent as needed.

The reaction temperature may generally range form $-100°$ C. to the boiling point of the solvent employed. It is, however, preferred to conduct the reaction in a range of form $-50$ to $50°$ C. The reaction time is generally from 0.1 to 1,000 hours.

Subsequent to the completion of the reaction, the target product can be extracted with a suitable solvent, and the solvent can then be driven off under reduced pressure to collect a crude product.

Purification can then be conducted by a usual method such as distillation, recrystallization or silica gel column chromatography to isolate the target compound (5) in a pure form.

It is to be noted that the intermediate (A) used as the starting material in the above-described production process can be synthesized by the following process.

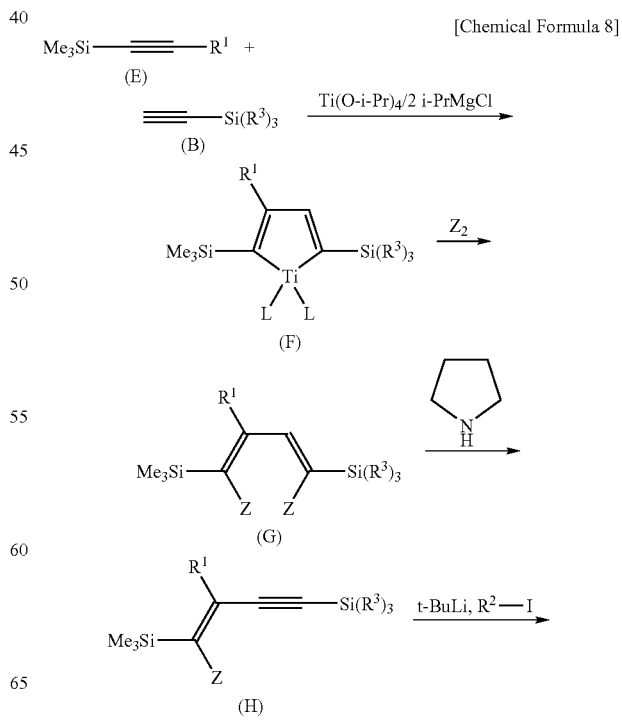

[Chemical Formula 8]

-continued

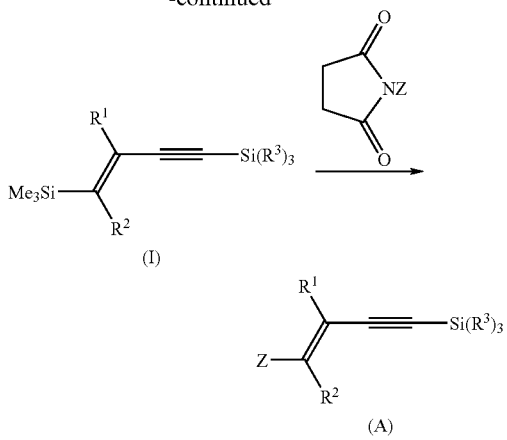

wherein $R^1$, $R^2$, $R^3$ and Z have the same meanings as defined above, Me represents a methyl group, and Bu represents a butyl group.

Described specifically, a titanacyclopentadiene intermediate (F), which has been obtained by a selective cross-coupling reaction of an internal acetylene (E) and a terminal acetylene (B) with a divalent titanium reagent $Ti(Oi-Pr)_4/2i-PrMgCl$, is treated with iodine or bromine to obtain a 1,4-dihalo-1,3-diene derivative (G) (see J. Org. Chem., 63, 10060 (1998) and J. Am. Chem. Soc., 121, 7342 (1999)).

A base is caused to act on the 1,4-dihalo-1,3-diene derivative (G) to perform a dehydrohalogenation reaction so that the 1,4-dihalo-1,3-diene derivative (G) is converted into an intermediate (H). After the intermediate (H) is alkylated to derive an enyne compound (I), the silyl group can be substituted with a halogen to produce the target intermediate (A) (see J. Org. Chem., 63, 10060 (1998)).

(2) Fabrication Process of an Electrode Junction with an Enediyne Compound

[Chemical Formula 9]

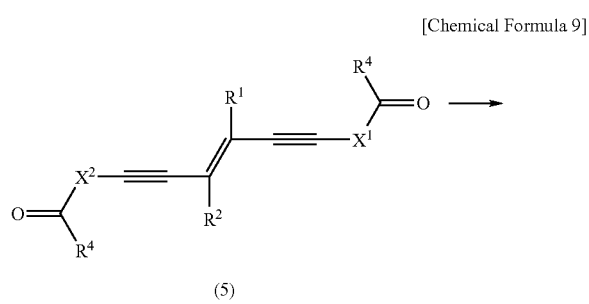

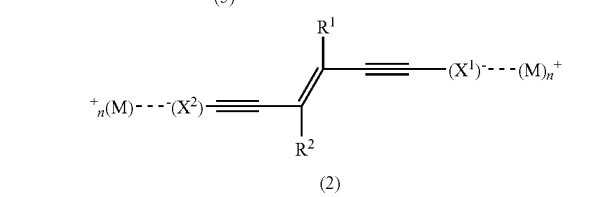

wherein $R^1$, $R^2$, $R^4$, X, M and n have the same meanings as defined above.

After the enediyne compound (5) obtained as described above is hydrolyzed, a metal substrate is immersed in the resulting hydrolyzate solution to form a self-assembled film. Using a tip, the self-assembled film is then bridged to the metal substrate under an ultra-vacuum, thereby making it possible to obtain a target electrode junction (monomolecular conductive complex) (2).

The junction between the single molecule and the metal can be formed, for example, by the scanning tunneling microscope (hereinafter called "STM") break-junction technique.

The term "STM break-junction technique" means a method that a metal tip is driven into a metal substrate having a conductive self-assembled film formed as described above and the tip is then drawn out of the substrate at about 4 nm/sec to hold the molecule between two electrodes, one being the metal substrate and the other the metal tip, in the form of metal substrate-molecule-metal tip. That is, in the electrode junction obtained by the STM break-junction technique, one of the electrode is the metal substrate to the surface of which the molecule is chemically bound at one end or opposite ends thereof, and the other electrode is the STM tip.

It is to be noted that no particular limitation is imposed on the shape of the metal tip. It is possible to use, for example, a metal wire or the like, which has been subjected to machining by mechanical cutting or electrolytic polishing to have a sharpened tip. As the preparation of a clean tip is essential for the measurement, it is necessary to apply processing, such as baking under an ultra high vacuum or argon ion sputtering, to the probe.

EXAMPLES

The present invention will hereinafter be described more specifically based on Examples. However, the present invention is not limited to the following Examples.

The following analysis systems and analysis conditions were adopted in the Examples.

$^1$H-NMR (300 MHz) and $^{13}$C-NMR (75 MHz) Measurement Conditions:

| Apparatus: | "Varian Gemini-2000" |
|---|---|
| Measurement solvent: | $CDCl_3$ |
| Reference material: | Tetramethylsilane (TMS) (δ 0.0 ppm for $^1$H) $CDCl_3$ (δ 77.0 ppm for $^{13}$C) |
| IR measurement apparatus: | "JASCO A-230" |
| Element analyzer: | "ELEMENTAR VARIO-EL" |

Example 1

[1] Synthesis of trans-enediyne dithioacetate Compound 14

(1) Synthesis of 1,4-diiodo-1,3-diene Compound 8

[Chemical Formula 10]

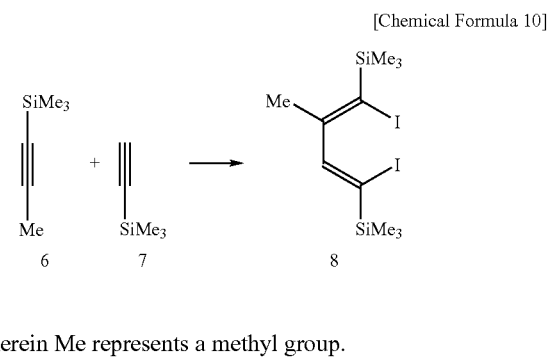

wherein Me represents a methyl group.

Tetra-i-propoxytitanium (18.5 mL, 62.5 mmol) was added to a solution of 1-trimethylsilyl-1-propyne 6 (5.61 g, 50.0 mmol) in diethyl ether (500 mL), then the resulting mixture was cooled to −78° C., followed by the gradual addition of i-propylmagnesium chloride (2.23 mol/L ether solution, 56.1 mL, 125 mmol). The thus-obtained mixture was warmed to −50° C over 30 minutes, and was then stirred at that temperature for 2 hours. Trimethylsilylacetylene 7 (8.20 mL, 58.0 mmol) was added, followed by stirring at −50° C. for 3 hours.

Iodine (31.8 g, 125 mmol) was added, and the thus-obtained mixture was stirred at room temperature for 2 hours. Water was added at 0° C. to the reaction mixture, then "CELITE" filtration was performed.

Diethyl ether and a saturated aqueous solution of sodium thiosulfate were added. After confirming disappearance of excess iodine, the mixture was separated into two layers and then washed with a saturated aqueous sodium chloride solution. The organic layer was dried over anhydrous magnesium sulfate. Subsequent to filtration, the filtrate was concentrated under reduced pressure. The resultant crude product was confirmed with NMR, and was provided for the next reaction.

(2) Synthesis of cis-silylated haloenyne Compound 9

[Chemical Formula 11]

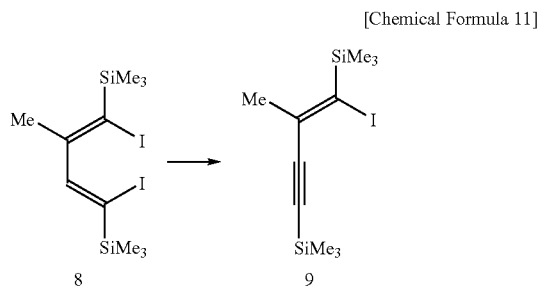

wherein Me represents a methyl group.

To a solution of the above-obtained crude product of 1,4-diiodo-1,3-diene compound 8 in THF (250 mL), pyrrolidine (20.8 mL, 250 mmol) was added at 0° C., followed by stirring at room temperature for 12 hours. Water was added at 0° C. to the reaction mixture to effect quenching. The water layer was extracted with diethyl ether, the extract was washed with a saturated aqueous sodium chloride solution, and then, the organic layer was dried over anhydrous magnesium sulfate. Subsequent to filtration, the filtrate was concentrated under reduced pressure to collect a crude product. The crude product was purified with chromatography on a silica gel column (hexane) to obtain a cis-haloenyne compound 9 with a yield of 32% (5.39 g) through the two steps.

$^1$H NMR (300 MHz, CDCl$_3$) δ 2.04 (s, 3H), 0.29 (s, 9H), 0.23 (s, 9H).

$^{13}$C NMR (75 MHz, CDCl$_3$) δ 138.38, 116.46, 110.69, 98.97, 23.19, 1.47, −0.32.

IR (neat) 2959, 2898, 2153, 1544, 1408, 1251, 1201, 842, 759, 696 cm$^{-1}$.

Anal. Calcd for C$_{11}$H$_{21}$ISi$_2$: C, 39.28; H, 6.29. Found: C, 39.10; H, 6.31.

(3) Synthesis of bis-silylated enyne Compound 10

[Chemical Formula 12]

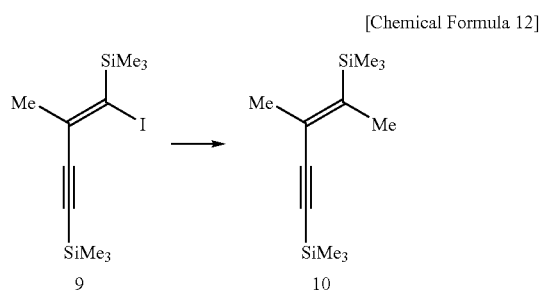

wherein Me represents a methyl group.

The cis-silylated haloenyne compound 9 (2.13 g, 6.34 mmol) obtained in Example 1[1](2) was dissolved in diethyl ether (21 mL), and the resulting solution was cooled to −78° C.

t-Butyl lithium (1.6 M/pentane solution, 9.89 mL, 15.9 mmol) was added, and the resultant mixture was stirred for 1 hour. Iodomethane (1.58 mL, 25.4 mmol) was added dropwise. The thus-obtained mixture was warmed to room temperature, at which it was stirred for 6 hours. Water was added at 0° C. to the reaction mixture to effect quenching.

The water layer was extracted with diethyl ether, the extract was washed with a saturated aqueous sodium chloride solution, and then, the organic layer was dried over anhydrous magnesium sulfate. Subsequent to filtration, the filtrate was concentrated under reduced pressure to collect a crude product. The crude product was confirmed with NMR, and was then provided for the next reaction.

(4) Synthesis of trans-haloenyne Compound 11

[Chemical Formula 13]

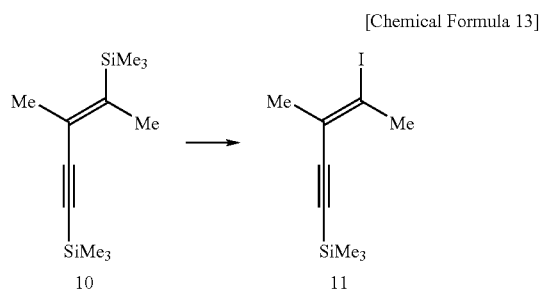

wherein Me represents a methyl group.

The above-obtained crude product of the bis-silylated enyne compound 10 was dissolved in dichloromethane (32 mL), followed by the addition of N-iodosuccinimide (2.80 g, 12.7 mmol). With the reaction vessel blocked off the light with an aluminum foil, the resultant mixture was stirred at room temperature for 2 hours. A saturated aqueous solution of sodium thiosulfate was added at 0° C. to the reaction mixture to effect quenching. The water layer was extracted with dichloromethane, the extract was washed with a saturated aqueous sodium chloride solution, and then, the organic layer was dried over anhydrous magnesium sulfate. Subsequent to filtration, the filtrate was concentrated under reduced pressure to collect a crude product. The crude product was purified with chromatography on a silica gel column (hexane) to obtain a trans-haloenyne compound 11 with a yield of 68% (1.19 g) through the two steps.

$^1$H NMR (300 MHz, CDCl$_3$) δ 2.78-2.72 (m, 3H), 2.05-1.95 (m, 3H), 0.20 (s, 9H).

$^{13}$C NMR (75 MHz, CDCl$_3$) δ 123.73, 110.05, 101.87, 99.30, 32.56, 28.27, −0.18.

IR (neat) 2959, 2140, 1251, 1072, 864, 760 cm$^{-1}$.

Anal. Calcd for C$_9$H$_{15}$ISi: C, 38.85; H, 5.43. Found: C, 39.02; H, 5.07.

(5) Synthesis of trans-bis-silylated enediyne Compound 12

[Chemical Formula 14]

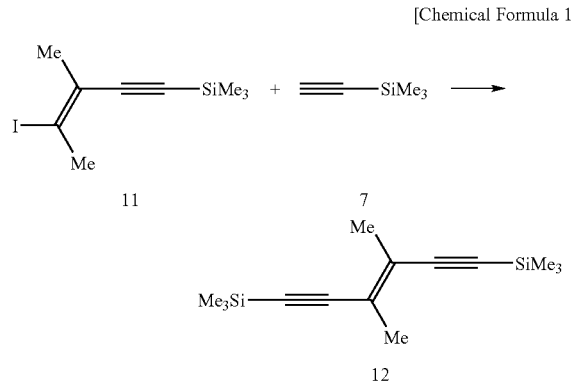

wherein Me represents a methyl group.

Tetrakistriphenylphosphine palladium (31.2 mg, 0.0270 mmol) and cuprous iodide (10.2 mg, 0.0539 mmol) were added at room temperature to a solution of the trans-haloenyne compound 11 (150 mg, 0.540 mmol), which had been obtained in Example 1[1](4), in deaerated triethylamine (1.3 mL), then a solution of trimethylsilylacetylene 7 (0.152 mL, 1.08 mmol) in deaerated THF (5.4 mL) was added dropwise. The reaction solution was stirred at room temperature for 12 hours. Water was added at 0° C. to the reaction mixture to effect quenching. The water layer was extracted with diethyl ether, the extract was washed with a saturated aqueous sodium chloride solution, and then, the organic layer was dried over anhydrous magnesium sulfate. Subsequent to filtration, the filtrate was concentrated under reduced pressure to collect a crude product. The crude product was purified with chromatography on a silica gel column (hexane) to obtain a trans-bis-silylated enediyne compound 12 with a yield of 98% (110 mg).

$^1$H NMR (300 MHz, CDCl$_3$) δ 2.01 (s, 6H), 0.20 (s, 18H).

$^{13}$C NMR (75 MHz, CDCl$_3$) δ 125.62, 105.16, 103.73, 21.12, −0.12.

IR (neat) 2960, 2140, 1251, 1194, 939, 842, 760, 699 cm$^{-1}$

Anal. Calcd for C$_{14}$H$_{24}$Si$_2$: C, 67.66; H, 9.73. Found: C, 67.47; H, 9.64.

(6) Synthesis of trans-dimethylenediyne 13

[Chemical Formula 15]

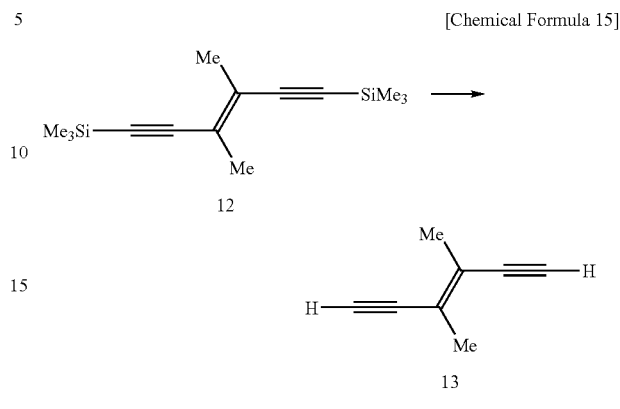

wherein Me represents a methyl group.

The trans-bis-silylated enediyne compound 12 (0.273 g, 1.10 mmol), which had been obtained in Example 1[1](5), was dissolved in THF (2.2 mL). After the thus-obtained solution was cooled to 0° C., tetrabutylammonium fluoride (1.0 M/THF solution, 3.31 mL, 3.31 mmol) was added, and the resulting mixture was stirred for 1 hour. Water was added to the reaction mixture to effect quenching. After the water layer was extracted with a small amount of hexane, the organic layer was dried over anhydrous magnesium sulfate. The resultant organic layer was filtered with a small amount of silica gel, and the filtrate was provided for the next reaction without concentration.

(7) Synthesis of trans-enediynyl dithioacetate ester Compound 14

[Chemical Formula 16]

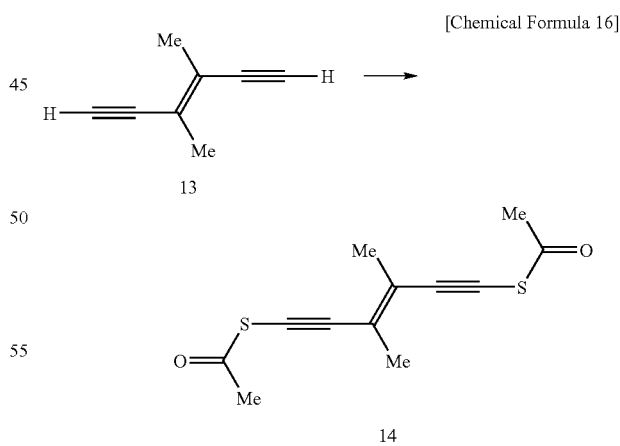

wherein Me represents a methyl group.

The above-obtained filtrate, which contained the trans-dimethylenediyne 13, was cooled to −50° C., followed by the dropwise addition of n-butyl lithium (1.59 M/hexane solution, 1.52 mL, 2.42 mmol). The reaction mixture was stirred at −50° C. for 1 hour. After the reaction mixture was warmed to −30° C., sulfur (0.106 g, 3.31 mmol) was added. The reaction mixture was warmed to room temperature, at which the reaction mixture was stirred for 2 hours, followed by cooling down to −50° C. again. Acetyl chloride (0.274 mL, 3.86 mmol) was added to the reaction mixture, and the resulting mixture was warmed to room temperature, followed by stirring for 12 hours. Water was added at 0° C. to the reaction mixture to effect quenching. The water layer was extracted with diethyl ether, the extract was washed with a saturated aqueous sodium chloride solution, and then, the organic layer was dried over anhydrous magnesium sulfate. Subsequent to filtration, the filtrate was concentrated under reduced pressure to collect a crude product. The crude product was purified with chromatography on a silica gel column (hexane/diethyl ether) to obtain a trans-enediynyl acetate compound 14 with a yield of 10% (0.0291 g) through the two steps.

$^1$H NMR (300 MHz, CDCl$_3$) δ 2.48 (s, 6H), 2.13 (s, 6H).

$^{13}$C NMR (75 MHz, CDCl$_3$) δ 191.77, 125.02, 103.29, 80.44, 29.58, 20.88.

IR (neat) 2925, 2855, 1739, 1461, 1251, 1110, 946, 841 cm$^{-1}$

Anal. Calcd for C$_{12}$H$_{12}$O$_2$S$_2$: C, 57.11; H, 4.79. Found: C, 57.39; H, 4.50.

[2] Synthesis of enediyne-dithiol:gold Complex

The trans-enediynyl thioacetate compound 14 obtained in Example 1 [1] was dissolved in toluene to give a mole concentration of 2 mmol/L. A single droplet of 30% ammonia solution was added to the solution in order to hydrolyze the compound. After the solution was left for 1 hour, a substrate of a (111) plane of gold was immersed for 1 minute in the solution to prepare an enediyne-dithiol:gold complex. Confirmation of the enediyne-dithiol:gold complex was performed before the below-described characteristic assessment of by scanning via a vacuum gap its surface with a tip obtained by subjecting a mechanically-cut gold wire to baking or sputtering processing.

[3] Characteristic Assessment of the enediyne-dithiol:gold Complex

A mechanically-cut gold wire was subjected to baking and sputtering processing, and was used as a tip. The tip was driven into the substrate fabricated as described above, and was then drawn out of the substrate at about 4 nm/sec. In the course of the draw-out, distances between the tip and the metal substrate and variations in current value were plotted along the abscissa and the ordinate, respectively, to make a graph. The above procedure was repeated to observe the graphs.

As a result, it was possible to observe the phenomenon that the current value varied stepwise as shown in FIG. 1. Taking the lowest value as a fiducial value at horizontally flat sections in the stepwise currents, steps concentrated around the current value of the fiducial value, and steps also concentrated around its two and three multiples. These quantized conductance steps can be considered to correspond to the conductances through 1 molecule, 2 molecules and 3 molecules, respectively. A conductance value which can be calculated from the fiducial value of the current was, therefore, determined to be the intrinsic conductance value which the molecule has. The specific fiducial value was about 8.4 nA at 0.1 V, and the conductance value of the enediyne-dithiol was calculated to be $1.1 \times 10^{-3}$ G$_0$.

Comparative Example 1

[1] Synthesis of 1,6-hexanedithiol:gold Complex

Concerning molecules of 1,6-hexandithiol, a gold substrate was immersed for 1 minute in its 1 mmol/L ethanol solution to prepare a gold complex. Confirmation of the gold complex was performed in a similar manner as in Example 1 [2].

[2] Characteristic Assessment of the 1,6-hexanedithiol: gold Complex

Figure 2:
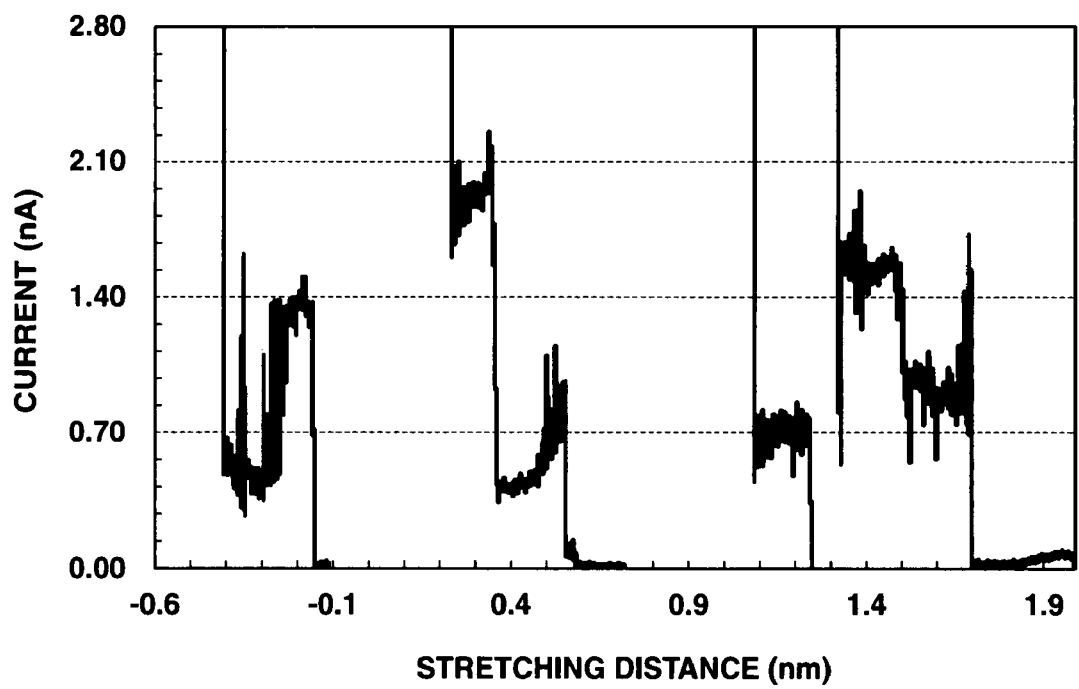
FIG. 2 A graph showing conductance steps of 1,6-hexanedithiol of Comparative Example 1.

The procedure of Example 1 [3] was likewise repeated in the presence of 1,6-hexanedithiol to obtain a graph as shown in FIG. 2. The fiducial value was about 0.73 nA at 0.1 V, and the conductance value of 1,6-hexanedithiol was calculated to be $9.4 \times 10^{-5}$ G$_0$.

As described above, molecules of the trans-enediynyl dithioacetate compound 14 having the π-conjugated system and obtained above in Example 1 [1] have been ascertained to have electrical conductivity as high as 10 times or more than those of 1,6-hexanedithiol formed of a saturated hydrocarbon.

The invention claimed is:

1. An enediyne compound characterized by being represented by the formula (1):

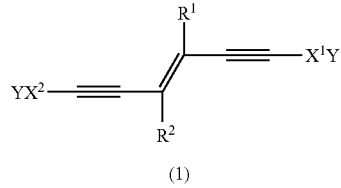

(1)

wherein:

R$^1$ and R$^2$ each independently represent a hydrogen atom, halogen atom, cyano group, nitro group, hydroxyl group, mercapto group, amino group, formyl group, carboxyl group, C$_1$ to C$_{10}$ alkyl group, halo C$_1$ to C$_{10}$ alkyl group, C$_1$ to C$_{10}$ alkenyl group, C$_1$ to C$_{10}$ alkynyl group, C$_1$ to C$_{10}$ alkoxy group, C$_1$ to C$_{10}$ alkylthio group, mono C$_1$ to C$_{10}$ alkyl amino group, di C$_1$ to C$_{10}$ alkyl amino group, tri C$_1$ to C$_{10}$ alkyl silyl group, C$_1$ to C$_{10}$ alkyl carbonyl group, C$_1$ to C$_{10}$ alkoxy carbonyl group, C$_1$ to C$_{10}$ alkoxy C$_1$ to C$_{10}$ alkyl group, C$_1$ to C$_{10}$ alkyl carbonyl C$_1$ to C$_{10}$ alkyl group, C$_1$ to C$_{10}$ alkyloxy carbonyl C$_1$ to C$_{10}$ alkyl group, di C$_1$ to C$_{10}$ alkyl amino C$_1$ to C$_{10}$ alkyl group, nitro C$_1$ to C$_{10}$ alkyl group, W-substituted or unsubstituted aryl group, W-substituted or unsubstituted arylalkyl group, W-substituted or unsubstituted aryloxy group, W-substituted or unsubstituted arylthio group, W-substituted or unsubstituted monoarylamino group, W-substituted or unsubstituted diarylamino group, W-substituted or unsubstituted tri C$_1$ to C$_{10}$ aryl silyl group, W-substituted or unsubstituted arylcarbonyl group, or W-substituted or unsubstituted aryloxycarbonyl group, X$^1$ and X$^2$ each independently represent a sulfur atom or selenium atom, Y represents a hydrogen atom, C$_1$ to C$_{10}$ alkyl group, C$_1$ to C$_{10}$ alkoxy group, C$_1$ to C$_{10}$ alkyl carbonyl group, C$_1$ to C$_{10}$ alkoxy carbonyl group, W-substituted or unsubstituted aryl group, W-substituted or unsubstituted arylalkyl group, W-substituted or unsubstituted C$_1$ to C$_{10}$ aryl carbonyl group, or W-substituted or unsubstituted C$_1$ to C$_{10}$ aryloxy carbonyl group, W represents a halogen atom, cyano group, nitro group, hydroxyl group, mercapto group, amino group, formyl group, carboxyl group, C$_1$ to C$_{10}$ alkyl group, halo C$_1$ to C$_{10}$ alkyl group, C$_1$ to C$_{10}$ alkenyl group, C$_1$ to C$_{10}$ alkynyl group, $C_1$ to $C_{10}$ alkoxy group, $C_1$ to $C_1$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, Z-substituted or unsubstituted phenyl group, Z-substituted or unsubstituted naphthyl group, or Z-substituted or unsubstituted biphenyl group, and Z represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, or $C_1$ to $C_{10}$ alkoxy carbonyl group.

2. The enediyne compound according to claim 1, wherein:

$R^1$ and $R^2$ each independently represent a hydrogen atom, halogen atom, cyano group, nitro group, $C_1$ to $C_{10}$ alkyl group, halo $C_1$ to $C_{10}$ alkyl group, $C_1$ to $C_{10}$ alkoxy group, di $C_1$ to $C_{10}$ alkyl amino group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above), $X^1$ and $X^2$ each independently represent a sulfur atom, and Y represents a hydrogen atom, $C_1$ to $C_{10}$ alkyl group, $C_1$ to $C_{10}$ alkoxy group, $C_1$ to $C_{10}$ alkyl carbonyl group, $C_1$ to $C_{10}$ alkoxy carbonyl group, W-substituted or unsubstituted aryl group, W-substituted or unsubstituted arylalkyl group, W-substituted or unsubstituted $C_1$ to $C_{10}$ aryl carbonyl group, or W-substituted or unsubstituted $C_1$ to $C_{10}$ aryloxy carbonyl group (in which W has the same meaning as defined above).

3. The enediyne compound according to claim 2, wherein:

$R^1$ and $R^2$ each independently represent a hydrogen atom, $C_1$ to $C_{10}$ alkyl group, halo $C_1$ to $C_{10}$ alkyl group, $C_1$ to $C_{10}$ alkoxy $C_1$ to $C_{10}$ alkyl group, $C_1$ to $C_{10}$ alkyloxy carbonyl $C_1$ to $C_{10}$ alkyl group, di $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above), and Y represents a hydrogen atom or $C_1$ to $C_1$ alkyl carbonyl group.

4. An electrode junction represented by a formula (2) characterized in that an enediyne compound is covalently or coordinatively bonded at opposite ends thereof with a surface of a metal, metal oxide or semiconductor:

[Chemical Formula 2]

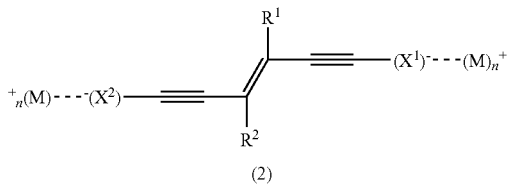

(2)

wherein:

$R^1$ and $R^2$ each independently represent a hydrogen atom, halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, W-substituted or unsubstituted aryl group, W-substituted or unsubstituted arylalkyl group, W-substituted or unsubstituted aryloxy group, W-substituted or unsubstituted arylthio group, W-substituted or unsubstituted monoarylamino group, W-substituted or unsubstituted diarylamino group, W-substituted or unsubstituted triarylsilyl group, W-substituted or unsubstituted arylcarbonyl group, or W-substituted or unsubstituted aryloxycarbonyl group, $X^1$ and $X^2$ each independently represent a sulfur atom or selenium atom, W represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, $C_1$ to $C_{10}$ alkoxy carbonyl group, Z-substituted or unsubstituted phenyl group, Z-substituted or unsubstituted naphthyl group, or Z-substituted or unsubstituted biphenyl group, Z represents a halogen atom, cyano group, nitro group, hydroxyl group, mercapto group, amino group, formyl group, carboxyl group, $C_1$ to $C_{10}$ alkyl group, halo $C_1$ to $C_{10}$ alkyl group, $C_1$ to $C_{10}$ alkenyl group, $C_1$ to $C_{10}$ alkynyl group, $C_1$ to $C_{10}$ alkoxy group, $C_1$ to $C_{10}$ alkylthio group, mono $C_1$ to $C_{10}$ alkyl amino group, di $C_1$ to $C_{10}$ alkyl amino group, tri $C_1$ to $C_{10}$ alkyl silyl group, $C_1$ to $C_{10}$ alkyl carbonyl group, or $C_1$ to $C_{10}$ alkoxy carbonyl group, and each M is a metal atom derived from said metal, metal oxide or semiconductor, and represents Au, Ag, Cu, Pd, Fe, Hg, Ga or In.

5. The electrode junction according to claim 4, wherein:

$R^1$ and $R^2$ each independently represent a hydrogen atom, halogen atom, cyano group, nitro group, $C_1$ to $C_{10}$ alkyl group, $C_1$ to $C_{10}$ haloalkyl group, $C_1$ to $C_{10}$ alkoxy group, $C_1$ to $C_{10}$ dialkylamino group, $C_1$ to $C_{10}$ alkoxy $C_1$ to $C_{10}$ alkyl group, $C_1$ to $C_{10}$ alkyl carbonyl $C_1$ to $C_{10}$ alkyl group, $C_1$ to $C_{10}$ alkyloxy carbonyl $C_1$ to $C_{10}$ alkyl group, di $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or lo unsubstituted aryl group (in which W has the same meaning as defined above), and $X^1$ and $X^2$ each independently represent a sulfur atom.

6. The electrode junction according to claim 5, wherein:

$R^1$ and $R^2$ each independently represent a hydrogen atom, $C_1$ to $C_{10}$ alkyl group, halo $C_1$ to $C_{10}$ alkyl group, $C_1$ to $C_{10}$ alkoxy $C_1$ to $C_{10}$ alkyl group, $C_1$ to $C_{10}$ alkyloxy carbonyl $C_1$ to $C_{10}$ alkyl group, di $C_1$ to $C_{10}$ alkyl amino $C_1$ to $C_{10}$ alkyl group, nitro $C_1$ to $C_{10}$ alkyl group, or W-substituted or unsubstituted aryl group (in which W has the same meaning as defined above).

7. The electrode junction according to claim 6, wherein:

said enediyne compound is covalently or coordinatively bonded at said opposite ends thereof with a surface of a metal or metal oxide, and said each M is a metal atom derived from said metal or metal oxide, and represents Au, Ag, Cu, Pd, Fe, Hg, Ga or In.

8. The electrode junction according to claim 7, wherein:

said enediyne compound is covalently or coordinatively bonded at said opposite ends thereof with a surface of a metal, and said each M is a metal atom derived from said metal, and represents Au, Ag, Cu, Pd, Fe, Hg, Ga or In.

\* \* \* \* \*